(12) United States Patent
Calzada et al.

(10) Patent No.: US 7,168,165 B2
(45) Date of Patent: Jan. 30, 2007

(54) FABRICATION OF ELECTRICAL MEDICAL LEADS EMPLOYING MULTI-FILAR WIRE CONDUCTORS

(75) Inventors: Javier E. Calzada, Rio Piedras, PR (US); Jaime Leon, Villalba, PR (US); Jorge L. Santiago Torres, Villalba, PR (US)

(73) Assignee: Medtronic, Inc., Minneapolis, MN (US)

( * ) Notice: Subject to any disclaimer, the term of this patent is extended or adjusted under 35 U.S.C. 154(b) by 144 days.

(21) Appl. No.: 11/073,789

(22) Filed: Mar. 7, 2005

(65) Prior Publication Data

US 2006/0200216 A1    Sep. 7, 2006

(51) Int. Cl.
*H01R 43/02* (2006.01)
*H01R 43/04* (2006.01)
*B23K 31/00* (2006.01)
*B23K 1/002* (2006.01)
*B23K 37/00* (2006.01)
*A61N 1/00* (2006.01)
*A61B 5/04* (2006.01)

(52) U.S. Cl. ............... 29/860; 29/867; 29/857; 228/180.5; 228/110.1; 228/4.5; 607/116; 607/119; 607/122; 607/129; 600/373; 600/374; 600/375; 600/377

(58) Field of Classification Search ............... 607/116, 607/119, 122, 123, 126, 127, 129–31; 600/373–5, 600/377; 174/90, 128.1, 160, 119 R; 29/854, 29/857, 860, 867; 228/180.5, 110, 4.5; 219/56.22, 219/56, 56.1

See application file for complete search history.

(56) References Cited

U.S. PATENT DOCUMENTS

| | | | |
|---|---|---|---|
| 3,333,045 A | 7/1967 | Fisher et al. | 174/20 |
| 4,640,983 A | 2/1987 | Comte | 174/119 R |
| 4,835,853 A | 6/1989 | Hirschberg | 29/854 |
| 4,950,866 A * | 8/1990 | Kojima et al. | 219/137 PS |
| 5,269,056 A | 12/1993 | Yang et al. | 29/879 |
| 5,545,932 A * | 8/1996 | Estop et al. | 307/104 |
| 5,584,873 A | 12/1996 | Shoberg et al. | 607/122 |
| 5,760,341 A | 6/1998 | Laske et al. | 174/126.2 |
| 5,876,430 A | 3/1999 | Shoberg et al. | 607/122 |
| 6,052,625 A | 4/2000 | Marshall | 607/122 |
| 6,285,910 B1 | 9/2001 | Verness et al. | 607/122 |
| 6,366,820 B1 | 4/2002 | Doan et al. | 607/122 |
| 6,697,675 B1 | 2/2004 | Safarevich et al. | 607/116 |

* cited by examiner

*Primary Examiner*—Robert E. Pezzuto
*Assistant Examiner*—Natasha Patel
(74) *Attorney, Agent, or Firm*—Paul H. McDowall; Girma Wolde-Michael

(57) ABSTRACT

During fabrication of an electrical medical lead, a cut end of a stranded wire conductor is subjected to electrical current sufficient to heat and weld the strands together upon discharge of a high voltage between the cut end and a ground metal plate formed of a material of the stranded wire conductor. The discharge of weld energy between the stranded wire cut end and the ground plate induces heat in the wire strands at the stranded wire cut end and the ground plate sufficient to transfer conductive material from the ground plate to fuse the wire strands together. The fusing inhibits unraveling of the wire strands at the fused cut end, whereby the insertion of the stranded wire cable through a lead body lumen and the connection of the fused stranded wire cut end to a further lead component, e.g., a proximal lead connector element or distal electrode, is facilitated.

19 Claims, 4 Drawing Sheets

200

200

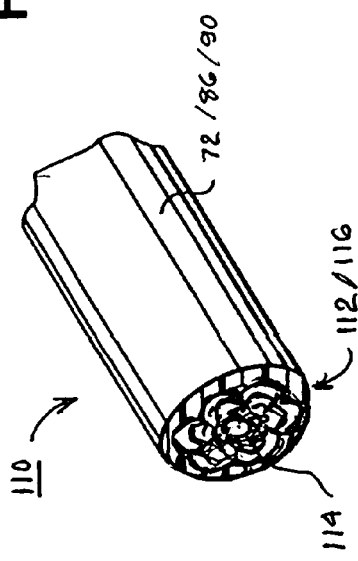
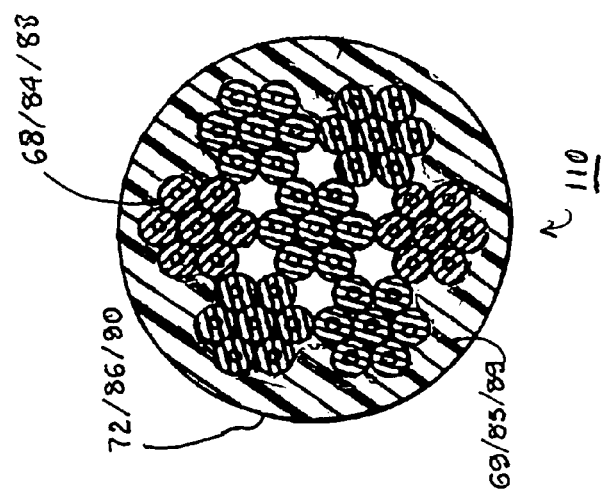
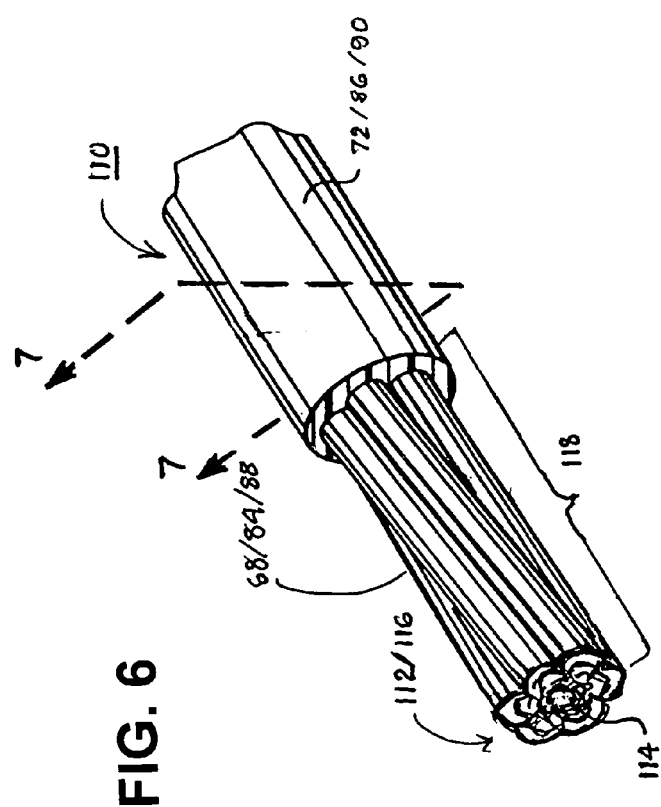

FABRICATION OF ELECTRICAL MEDICAL LEADS EMPLOYING MULTI-FILAR WIRE CONDUCTORS

FIELD OF THE INVENTION

The present invention relates to fabrication of implantable electrical medical leads intended for chronic implantation in the body and particularly to electrical medical leads for applying electrical stimulation to and/or sensing electrical activity of the body, particularly cardiac leads for applying electrical stimulation to and/or sensing electrical activity of the heart at one or more electrode positioned at a cardiac implantation site within a heart chamber or cardiac vessel adjacent a heart chamber.

BACKGROUND OF THE INVENTION

Implantable electrical medical stimulation and/or sensing leads intended for chronic implantation in the body are well known in the fields of cardiac stimulation and monitoring, including cardiac pacing and cardioversion/defibrillation (C/D), and in other fields of electrical stimulation or monitoring of electrical signals or other physiologic parameters.

An implantable cardioverter/defibrillator (ICD) implantable pulse generator (IPG) or pacemaker IPG or an implantable monitor is typically coupled to the heart through one or more of such cardiac leads having a lead body extending between a proximal lead connector assembly and a distal stimulation and/or sense electrode or electrodes. The lead body typically comprises one or more insulated conductive wire extending through a lead body lumen of insulating outer sleeve formed of silicone rubber or polyurethane. Each conductive wire couples a proximal lead connector element with a distal stimulation and/or sensing electrode. A cardiac lead having a single stimulation and/or sensing electrode at the lead distal end coupled to a single conductive wire extending to a single proximal connector element is referred to as a unipolar lead. A cardiac lead having two or more stimulation and/or sensing electrodes at the lead distal end and two or more conductive wires each extending to a proximal connector element is referred to as a bipolar lead or a multi-polar lead, respectively.

In use, the distal end of an endocardial lead is transvenously advanced from a surgically created subcutaneous access into a vein through the venous route and into a heart chamber or cardiac blood vessel, and typically active or passive fixation mechanisms are employed to maintain the distal electrodes at a selected implantation site. The distal end of an epicardial lead is advanced through the pericardial space to a site of active or passive fixation with the epicardium or myocardium. One or more connector element of the proximal lead connector assembly of such an endocardial and epicardial lead is connected with a connector header of the IPG or monitor that is then implanted at a subcutaneous site of the patient's body.

The heart beats approximately 100,000 times per day or over 30 million times a year, and each beat stresses the lead conductors and lead body insulation. Over the years of implantation, the lead conductors and insulation are subjected to cumulative mechanical stresses as well as material reactions that can result in degradation of the insulation or fractures of the lead conductors with untoward effects on performance and patient well being. The lead bodies of pacing and ICD leads are subjected to continuous stretching and flexing as the heart contracts and relaxes and are formed to be highly flexible, resilient, and durable employing durable, bio-compatible, lead conductor and insulator materials and structures.

In light of these considerations, lead conductors of early bipolar and bipolar cardiac pacing leads were formed employing a stainless steel or MP35N alloy wound into a wire coil threaded through a lead body lumen. The wire coils helped resist stress and ensuing fracture, and it was also possible to insert a stiffening stylet into the wire coil lumen to stiffen the lead body during transvenous implantation of endocardial pacing leads.

Many current endocardial pacing leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s). The number of separate lead conductors that can be incorporated in a lead body of a given diameter is limited in this coaxial winding approach.

Stiffening stylets were not typically used in implantation of epicardial pacing leads, and so stranded wire conductors, e.g., tinsel wire, were employed in the epicardial lead bodies of epicardial screw-in leads. In addition, highly flexible, silver core, drawn-brazed-strand (DBS) wire conductors were employed in early epicardial leads as described in U.S. Pat. No. 3,333,045. The '045 patent describes a silver core, DBS wire formed from a central silver filament surrounded by six silver-coated, stainless steel filaments that are drawn through a forming die while subjected to annealing heat to cause the silver coating to flow and braze the outer stainless steel and inner silver filaments together to form a DBS wire strand. Seven of the silver core DBS wire strands are then twisted around one another to form a 1×7 cable. Seven of the 1×7 cables are then wound and twisted together, preferably in a reverse spiral, to form a coiled, 7×7 strand, silver core, DBS wire cable (a 7×7 cable) or stranded wire conductor. Two of the 7×7 cables are loosely contained in lumens of a pair of silicone rubber tubes that are also filled with silicone fluid lubricant, and an outer silicone rubber sheath surrounds the pair of silicone rubber tubes.

This comparatively complex form of stranded wire conductor was not employed in clinically released unipolar and bipolar cardiac pacing leads for many years. However, more recently developed multi-polar cardiac leads, e.g., combined pacing and C/D leads, require an increased number of lead conductors in the lead body as well as high conductivity of at least the C/D lead conductors to more efficiently conduct C/D current. These needs have led to the development of lead bodies having multiple lead conductors including coiled wire conductors and substantially straight, high conductivity, stranded wire conductors that are electrically and mechanically coupled between a proximal connector element and to a distal electrode or terminal. Combinations of substantially straight, stranded wire conductors and at least one coiled wire conductor providing a stylet lumen are illustrated in commonly assigned U.S. Pat. Nos. 5,584,873, 6,052,625, and 6,285,910, for example. In these lead bodies, ETFE or PTFE sleeve insulators encase the stranded wire conductors, and a PTFE sleeve insulator surrounds the multi-filar, coiled wire, conductor. The insulated wire conductors are received in side-by-side lumens of an elongated lead body insulator that also incorporates elongated, empty, compression lumens.

The stranded wire conductors can take any of the forms disclosed in U.S. Pat. No. 5,760,341 and in the above-referenced '873 patent, for example. The number and composition of the individual strands of the stranded wire conductors vary as a function of the expected level of current to be carried and as a function of the material of which the wires or filaments are fabricated. High conductivity stranded wire cables are fabricated in a manner similar to that described in the above-referenced '045 patent employing silver core, MP35N wire filaments that are fabricated using a DBS fabrication process or a drawn filled tube (DFT) fabrication process well known in the art. In certain instances, the filaments are twisted into 1×7 strands, and then seven of the 1×7 strands are twisted about one another to form a substantially straight, 7×7 strand cable. In other instances nineteen of the filaments are twisted about one another to form a 1×19 cable. The 1×19 and 7×7 cables are then typically coated with an insulating layer to protect the cable strands and facilitate handling and provided for fabrication of cardiac leads.

During fabrication of a cardiac lead, it is necessary to make an electrical and mechanical connection of the 7×7 cable or 1×19 cable proximal end and distal end with a lead connector element and an electrode, respectively. It is necessary to cut the 7×7 cable or 1×19 cable into a cable length sufficient to extend through a lead body lumen and to make the electrical and mechanical connections and to trim away the insulation or otherwise expose a cable connection end section. The electrical and mechanical connections of the lead connector element and electrode to the exposed proximal and distal cable connection end sections are made employing mechanical crimping and/or laser welding techniques.

The exposed proximal and distal cable connection end sections can be damaged or can be frayed in the course of cutting or trimming the insulation from the 7×7 cable or 1×19 cable proximal end and distal end. The twisted strands or filaments can unravel and spread apart in the manner shown in the above-referenced '045 patent. It is suggested in the '045 patent that the cut ends of the 7×7 cable be "tinned" to prevent fraying during winding of the 7×7 cable into a helix. But, tinning with low melting temperature metals, other than perhaps molten silver, would introduce compounds or elements that would not necessarily be biocompatible and that could degrade the insulating materials or make the "tinned" ends difficult to mechanically and electrically attach to a connector element or electrode.

To avoid such problems, tinning is not used, and it has become standard practice to laser weld the 7×7 cable or 1×19 cable proximal and distal ends either in conjunction with the attachment to the lead connector element and electrode, respectively, or in a separate step. Butt welding techniques for laser welding tinned or un-tinned stranded wire ends to electrode pins are described, for example, in U.S. Pat. No. 5,269,056.

Laser welding the 7×7 cable or 1×19 cable proximal and distal ends to prevent fraying requires relatively bulky, expensive, precision laser welding equipment as can be seen from the three laser beam equipment disclosed in the above-referenced '056 patent that increases costs of fabrication.

Consequently, a need remains for low cost methods and equipment for adhering the filaments or strands of the cut ends of such stranded wire conductors together during fabrication of electrical medical leads that does not introduce impurities and provides consistent results.

SUMMARY OF THE INVENTION

In accordance with one aspect of the present invention, a cut end of such a stranded wire conductor is subjected to electrical current sufficient to heat and weld the strands together upon discharge of a high voltage between the stranded wire cut end and a ground metal plate. The discharge of weld energy from a weld energy source between the stranded wire cut end and the ground plate induces heat in the wire strands at the stranded wire cut end and the ground plate sufficient to melt and transfer conductive material from the ground plate into the interstices between the cut ends of the wire strands that solidifies to fuse the wire strands together. The fusing inhibits unraveling of the wire strands at the fused cut end, whereby the insertion of the stranded wire cable through a lead body lumen and the connection of the fused stranded wire cut end to a further lead component, e.g., a proximal lead connector element or distal electrode, is facilitated.

The weld energy source may comprise a high voltage discharge capacitor disposed between first and second discharge terminals and a current source for charging the high voltage capacitor to a weld voltage. The stranded wire conductor is coupled to a first discharge terminal, and the ground plate is coupled to the second discharge terminal. The high voltage capacitor is charged to a weld voltage, and the stranded wire cut end is moved into proximity with the ground plate causing the high voltage capacitor to discharge weld energy between the stranded wire cut end and the ground plate and arc weld the wire strands at the stranded wire cut end.

Advantageously, the weld energy required to transfer conductive material from the ground plate to the fused wire strands and fuse the wire strands together is relatively low due to the materials and the small diameters of the wire strands.

Furthermore, use of a material for the ground plate that is common to a material of the wire strands ensures that no contamination of the wire material is introduced in the transfer of material of the ground plate into the interstices of the wire strands.

The system and method of the present invention are particularly useful in fusing the cut ends of a plurality of wire strands, wherein at least a portion of the wire strands comprise a silver core wire.

In one preferred use of the system and method of the present invention, the wire strands and the ground plate are formed of MP35N alloy, and at least a portion or all of the wire strands are formed having a silver core.

In further preferred uses of the system and method of the present invention, the stranded wire conductor preferably comprises one of a 7×7 cable of wire strands or a 1×19 cable of wire strands, wherein at least a portion or all of the wire strands comprise a silver core wire.

Advantageously, the low electrical resistance of such silver core wires of the stranded wire conductor ensures that the current of the electrical arc between the stranded wire cut end and the ground plate is maximized without unduly heating the stranded wire conductor itself. Moreover, the diameter of the stranded wire conductor is not increased when the fusing takes place forming a weld mass.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 5 is a perspective view of a fused stranded wire cut end of a stranded wire conductor covered by insulation after welding of the wire strands in accordance with FIGS. 3 and 4;

FIG. 6 is a perspective view of a fused stranded wire cut end of the stranded wire conductor welded in accordance with the present invention and stripped of insulation in preparation to be attached to a lead component of the ICD lead of FIG. 1, for example; and FIG. 7 is an end cross-section taken along lines 7—7 of FIG. 6 illustrating a 7×7 cable formed of silver core MP35N wire strands.

DETAILED DESCRIPTION OF THE INVENTION

In the following detailed description, references are made to illustrative embodiments of methods and apparatus for carrying out the invention. It is understood that other embodiments can be utilized without departing from the scope of the invention.

Figure 1:
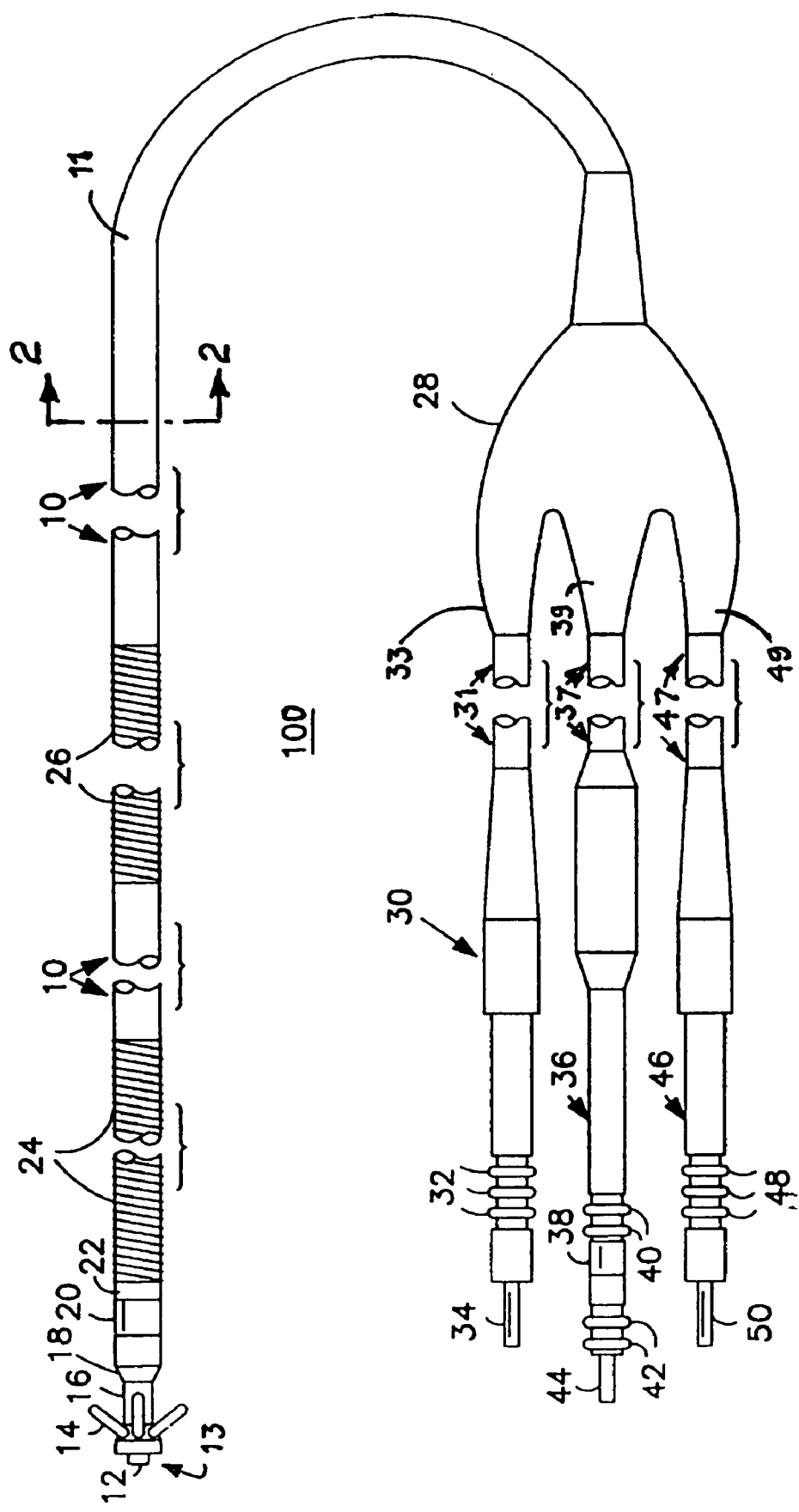
FIG. 1 is a conventional ICD lead in which the present invention may be advantageously practiced.

FIG. 1 therefore illustrates an exemplary cardiac lead 100, particularly and endocardial ICD lead of the type disclosed in the above-referenced '625 patent, in which the present invention is advantageously practiced. The lead 100 comprises an elongated lead body 10 extending between proximal lead connector assemblies 30, 36 and 46 and a lead body distal end 13. The lead body 10 is a complex structure having distinct proximal, intermediate, and distal regions having four lead lumens through which four electrical lead conductors that are electrically insulated from one another by the lead body insulator extend.

The distal region of the lead 100 includes a number of components, in this embodiment, including an elongated, open-coil, proximal cardioversion/defibrillation electrode 26, an elongated open-coil, distal cardioversion/defibrillation electrode 24 and a distal tip-ring assembly. The elongated open-coil structure retains flexibility in along the lengths of the proximal and distal cardioversion/defibrillation electrodes 26 and 24. The distal tip-ring assembly includes distal tip pace/sense electrode 12, tine sheath 16 carrying tines 14, tip-ring spacer component 18, ring-shaped pace/sense electrode 20, and ring-coil spacer component 22. The tine sleeve 16 fabricated of silicone rubber or a relatively softer polyurethane, and the tip-ring and ring-tip spacers 18 and 22 fabricated of relatively harder plastics, for example polyurethane having a Shore hardness of at least 75D, to provide a relatively rigid distal tip-ring assembly extending to the distal end of distal defibrillation The lead body insulator in the intermediate region comprises an elongated tubular lead body insulator 11, depicted in cross-section in FIG. 2. The lead body insulator 11 in the proximal region comprises a trifurcation sleeve 28 joining the proximal end of the elongated tubular lead body insulator 11 with the distal ends of insulating sleeves 31, 37 and 47 extending proximally from the trifurcation sleeve 28 to the proximal lead connector assemblies 30, 36, and 46, respectively. The trifurcation sleeve 28 includes an axially extending sleeve trunk 29 and trifurcation branches 33 and 49. Each of the sleeve trunk 29 and trifurcation branches 33 and 49 encloses a sleeve cavity or lumen that proximal segments of lead conductors extend through.

The lead body insulator 11 in the distal region is preferably fabricated of polyurethane, e.g., Pellethane 80A and Pellethane 55D, both products of Dow Chemical Co., and supports various insulating components and spacers supporting the distal array of components, e.g., electrodes 12, 20, 24 and 26 and the distal passive fixation tine sheath 16 as disclosed in detail in the above-referenced '625 patent. The lead body 10 comprises four mutually insulated, elongated conductors disposed within the lead body insulator 11 that are not visible in FIG. 1. Three of the insulated conductors are stranded wire conductors, each coupled to one of ring-shaped pace/sense electrode 20, elongated wire coil, distal cardioversion/defibrillation electrode 24 and elongated wire coil, proximal cardioversion/defibrillation electrode 26. A fourth, coiled wire, conductor is coupled to distal tip pace/sense electrode 12.

Connector assembly 30 supports a single connector pin 34, coupled to the conductor coupled to the distal cardioversion/defibrillation electrode 24, and is provided with sealing rings 32 to seal the connector assembly 30 within the connector bore of an ICD IPG connector header upon implantation. Similarly, connector assembly 46 is provided with a single connector pin 50 coupled to the conductor coupled to the proximal cardioversion/defibrillation electrode 26, and is provided with sealing rings 48 to seal the connector assembly 46 within a further connector bore of an ICD IPG connector header upon implantation. Connector assembly 36 takes the form of an IS-1 type connector assembly provided with a connector pin 44 coupled to the coiled conductor extending to tip pace/sense electrode 12 and a connector ring 38 coupled to a stranded wire conductor extending to ring-shaped pace/sense electrode 20. Sealing rings 40 and 42 provide a seal between connector pin 44 and connector ring 38 and seal the connector assembly 36 within the connector bore of the ICD IPG connector block upon implantation.

Figure 2:
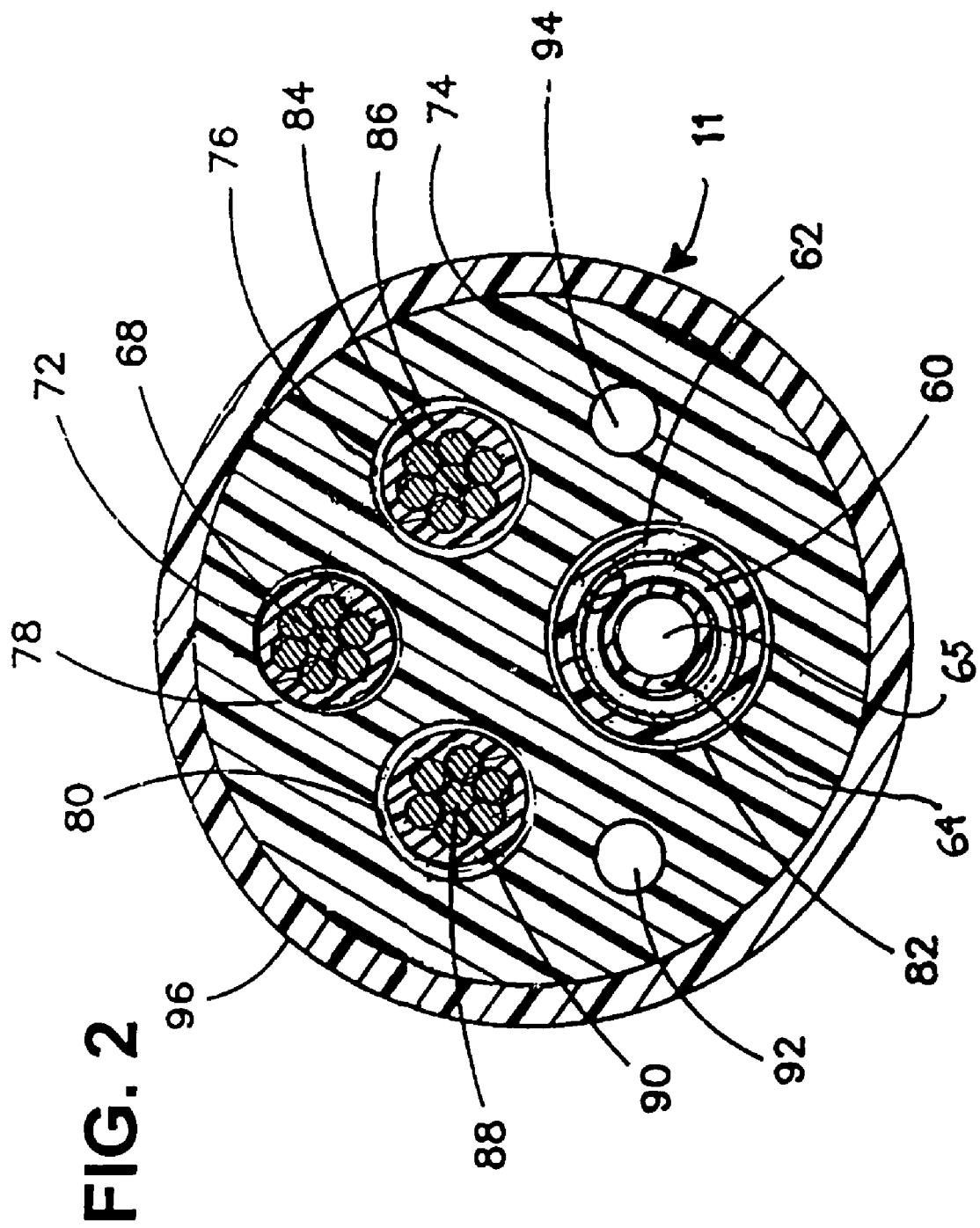
FIG. 2 is an end cross-section taken along lines 2—2 of FIG. 1 illustrating the lead lumens and lead conductors.

As shown in FIG. 2, the lead body insulator 11 that extends from the trifurcation sleeve 28 to the tip-ring assembly at the distal end of the lead is preferably formed of an extruded multi-lumen tube 74 surrounded by an overlay tube or sleeve 96. The multi-lumen tube 74 and sleeve 96 are fabricated of materials, e.g., extruded silicone rubber or polyurethane having a Shore hardness of 80A or 90A, or the like. The multi-lumen tube 74 is formed with conductor lumens 76, 78, 80, and 82 and stress or compression lumens 92 and 94 that are located diametrically opposite lumens 80 and 76. The compression lumens 92 and 94 are intended to relieve bending stresses and resist crushing forces as described in the above-referenced '873 patent. The sleeve 96 has approximately the same outer diameter and the same thickness as the wire from which the elongated wire coil cardioversion/defibrillation electrodes 24 and 26 are fabricated to make the elongated lead body 11 isodiametric between the lead body distal end and the trifurcation sleeve 28.

In the preferred embodiment, a coiled wire conductor 60 extends through a lumen 82 between distal tip pace/sense electrode 12 and connector pin 44 via trifurcation sleeve 28 and insulating sleeve 37. The coiled wire conductor 60 can be formed of a single coiled wire or can be formed of multi-filar stranded cable conductor wound into a coil, e.g., a 1×7 cable wound into a coil. In either case, the coiled wire conductor can comprise a plurality, e.g., four, of such single coiled wires or stranded coiled wires that are interlaced and wound to have a common diameter providing a central wire coil lumen as shown in U.S. Pat. No. 4,640,983, for example.

Referring to FIG. 2, an inner PTFE tube 64 having an inner tube lumen 65 is inserted into the lumen of the coiled wire conductor 60, and the coiled wire conductor 60 is encased within the lumen of an outer PTFE tube 62. The assembly of inner PTFE tube 64, the coiled wire conductor 60, and the outer PTFE tube 62 is fitted within the lumen 82 of elongated lead body 11 before the distal and proximal ends of coiled wire conductor 60 are coupled to the distal tip electrode 12 and proximal connector pin 44 (via trifurcation sleeve 28 and insulating sleeve 37), respectively.

Stranded wire conductors 84 and 88 extend through respective lumens 76 and 80 between the respective proximal and distal coil cardioversion/defibrillation electrodes 24 and 26 and respective connector pins 34 and 50 via trifurcation sleeve 28 and respective insulating sleeves 31 and 47. A further stranded wire conductor 68 extends through a fourth lumen 78 between the ring-shaped pace/sense electrode 20 and connector ring 38 via trifurcation sleeve 28 and insulating sleeve 37.

The stranded wire conductors 84 and 88 are depicted in FIG. 2 as 1×7 cables coated with thin insulating sheaths or layers 86 and 90, respectively. The insulated, stranded wire conductors 84 and 88 are inserted into respective lumens 76 and 80 and coupled to the respective proximal and distal coil cardioversion/defibrillation electrodes 24 and 26 and respective connector pins 34 and 50 via trifurcation sleeve 28 and respective insulating sleeves 31 and 47. The further stranded wire conductor 68 is also depicted as a 1×7 cable coated with an insulating sheath or layer 72 before being extended through fourth lumen 78 and coupled to the ring-shaped pace/sense electrode 20 and connector ring 38 via trifurcation sleeve 28 and insulating sleeve 37.

The insulating sheaths or layers 72, 86, 90 may be formed of a wide variety of biocompatible, biostable, non-conductive polymer materials including the aforementioned PTFE and ETFE, as well as other fluoropolymers, e.g., tetrafluoroethylene-hexafluoropropylene-vinylidene fluoride (THV), fluorinated ethylene propylene (FEP), polyfluoroalkoxyl (PFA), polychlorotrifluoroethylene (PCTFE), polyvinylidene fluoride (PVDF), and high durometer polyurethanes, e.g., Pellethane 75D and Tecothane 75D, etc.

The stranded wire conductors 68, 84, and 88 can take any of the forms described above and disclosed in the above-referenced '341 and '873 patents, for example. The number and fabrication of the individual strands of the stranded wire conductors 68, 84, and 88 may vary as a function of the expected level of current to be carried by the conductors between the proximal connector elements and the distal electrodes and as a function of their total cross-section area and the material of which they are fabricated. The stranded wire conductors 68, 84 and 88 can be fabricated in any of the known types, e.g., as the 1×7 cables depicted in FIG. 2 or as the above-described 1×19 or 7×7 cables, for example. Typically, the strands of such cables would be fabricated of MP35N nickel-cobalt alloy wire, preferably silver core MP35N wire formed in a DBS fabrication process or a DFT fabrication process as described above to provide increased conductivity. The present invention may be practiced employing wire cross-section and corresponding coiled insulating sheath cross-section shapes differing form the depicted circular shapes, e.g. elliptical or rectangular shapes.

The outer diameters of the insulating layers 72, 86, 90 and the outer insulating tube 62 are smaller than the diameters of the respective lumens 78, 76, 80, and 82, respectively, to facilitate assembly. It will be understood that the relative thicknesses of the ETFE or PTFE layer 72 to the diameter of lead conductor 68, the ETFE layers 86 and 90 to the respective lead conductors 84 and 88, and the inner and outer tubes 64 and 62 to the diameter of the coiled wire lead conductor 60 are exaggerated for ease of illustration in the drawing figures.

In the course of fabrication of an electrical medical lead, e.g., cardiac lead 100, it is necessary to cut the stranded wire conductors 68, 84, 88 and the coiled wire conductor 60 from stock to lengths that correspond to the lengths of the respective lumens 78, 76, 80, and 82. The stock stranded wire conductor is already insulated with an insulating coating of ETFE or PTFE as described above. The lead conductor lengths also have be cut long enough to extend through the lumens of the trifurcation sleeve 28 joining the proximal end of the elongated tubular lead body insulator 11 and through lumens of insulating sleeves 31, 37 and 47 extending proximally from the trifurcation sleeve 28 to make connections with connector elements of the proximal lead connector assemblies 30, 36, and 46, respectively. Similarly, the lead conductor lengths have to be cut long enough to extend a distal conductor segment to a connection site with the distal electrodes 12, 20, 24 or 26 that the lead conductor distal end is to be connected with. Generally, the connections are made by insertion of the lead conductor end portions into lumens of conductive electrode sleeve lumens or ring or pin connector element lumens where attachment is made by laser welding and/or crimping. See, for example, the connections of the proximal end portions of stranded wire lead conductors or cables to a connector pin, e.g., connector pins 34, 44 and 50, depicted in commonly assigned U.S. Pat. No. 5,876,430, and the connection of a stranded wire distal end to a distal ring electrode, e.g., ring electrode 20, depicted in the above-referenced '625 patent.

Figure 3:
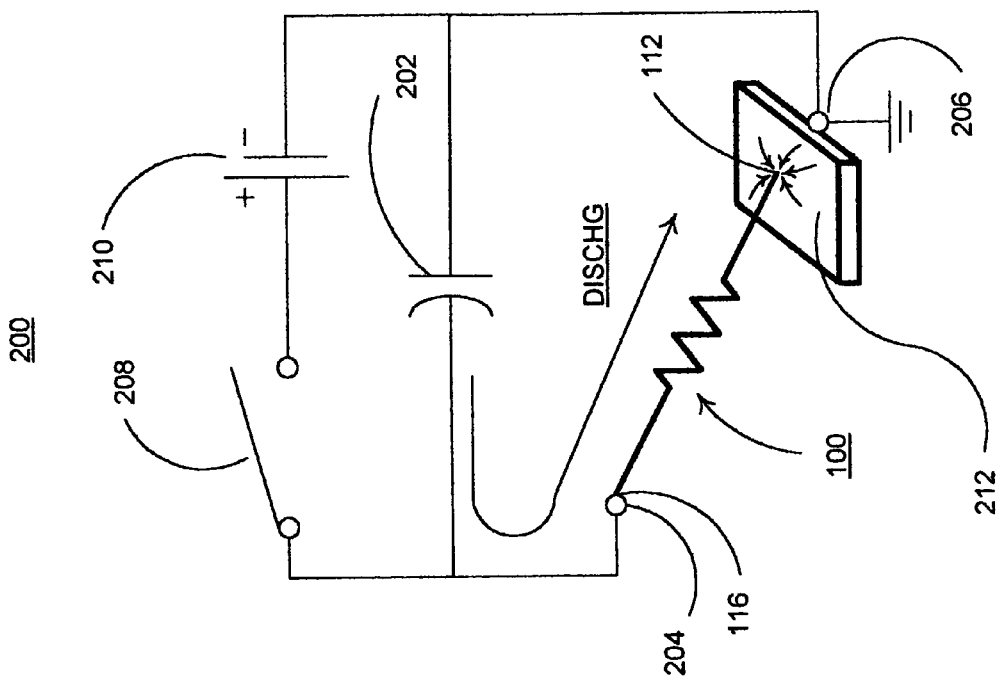
FIG. 3 is a schematic illustration of a capacitive discharge welding circuit of the present invention with the stranded wire cut end disposed away from the ground plate.
Figure 4:
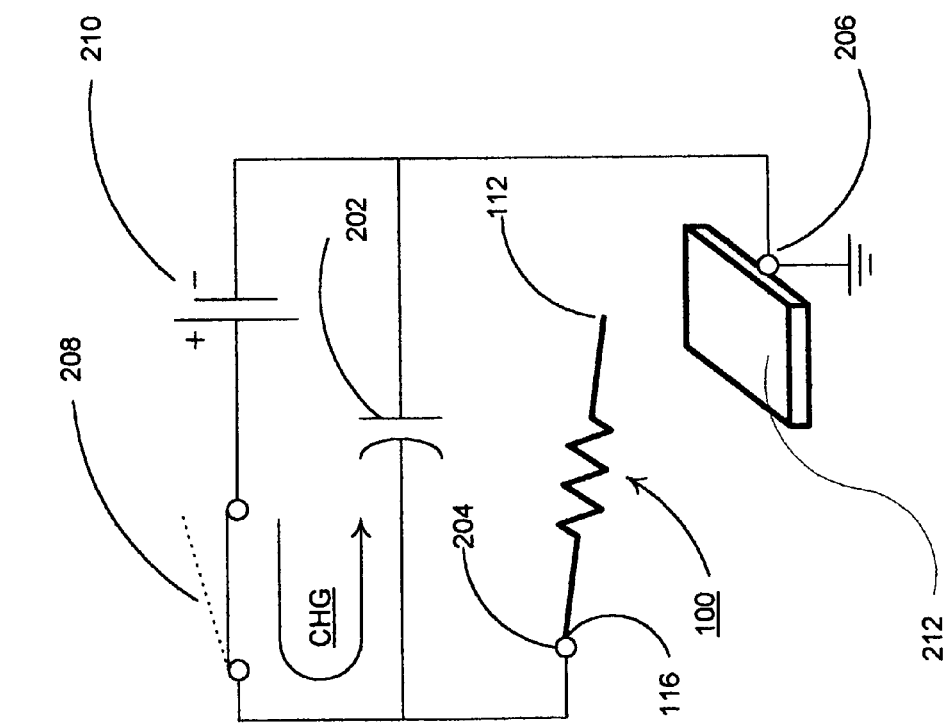
FIG. 4 is a schematic illustration of a capacitive discharge welding circuit of the present invention with the stranded wire cut end disposed against the ground plate initiating capacitive discharge of weld energy between the stranded wire cut end and the ground plate to transfer material of the ground plate and arc weld the wire strands to form the fused stranded wire cut end.

In reference to FIGS. 3 and 4, a cut length 110 of stranded wire conductor 68/84/88 is subjected to electrical current sufficient to heat and weld the strands together upon discharge of a high voltage between the stranded wire cut end 112 and a ground metal plate 212 formed of a material of the stranded wire conductor. The discharge of weld energy from a weld energy source between the stranded wire cut end 112 and the ground plate 212 induces heat in the wire strands at the stranded wire cut end 112 and the ground plate 212 sufficient to transfer conductive material from the ground plate 212 to the fused wire strands and fuse the wire strands together. It will be understood that both cut ends 112 and 116 of the cut length 110 of the stranded wire conductor 68/84/88 can be subjected to electrical current sufficient to heat and weld the strands together to form the weld mass 114 using the system and method depicted in FIGS. 3 and 4.

An exemplary cut length 110 of stranded wire conductor, e.g., stranded wire conductor 68 covered by insulating layer 72 or stranded wire conductor 84 covered by insulating layer 86 or stranded wire conductor 88 covered by insulating layer 90 is depicted in FIGS. 5–7. The stranded wire conductor 84/86/88 is depicted in FIG. 7 as comprising a 7×7 cable of silver core, MP35N alloy DBS or DFT wire strand. A weld mass or ball 114 formed at the cut end 112 or 116 from the melted materials of the wire strands and the material transferred from the ground plate 212. The weld mass 114 fills the interstices between the strands and does not increase the diameter of the stranded wire conductor 68/84/88. The fusing at the weld mass 114 inhibits unraveling of the wire strands at the fused cut end 112/116, whereby the insertion of the length 110 of stranded wire cable through a lead body lumen and the connection of the fused stranded wire cut end 112/116 to a further lead component, e.g., a proximal lead connector element or distal electrode, is facilitated.

The weld energy source of system 200 may comprise a high voltage discharge capacitor 202 disposed between first and second discharge terminals 204 and 206 and a current source e.g., a battery 210, operated through switch 208 for charging the high voltage capacitor 202 to a weld voltage. Switch 208 may be a mechanical SPST switch or may comprise an electronic switch, and the system 200 may optionally include a DC-DC converter to charge the high voltage capacitor 202 to a voltage exceeding the voltage of battery 210.

In FIG. 3, one cut end 116 of the cut length 110 of stranded wire conductor 68/84/88 is stripped of the insulating coating 72/86/90 and coupled by a clamp, for example, to the first discharge terminal 204, and the ground plate 212 is coupled to the second discharge terminal 206. The stranded wire cut end 112 to be arc welded to form the weld mass 114 is disposed away from the ground plate 212. The switch 208 is moved from its open position to a closed position to charge the high voltage capacitor 202 to a weld voltage by current flowing from battery 210. The switch 208 is moved back to its open position when the high voltage capacitor 202 is charged to the battery voltage.

In FIG. 4, the stranded wire cut end 112 to be arc welded to form the weld mass 114 is brought into close proximity or contact with the ground plate 212 to initiate discharge of the weld energy of the high voltage capacitor 202 through the stranded wire length 110. An arc of electric current flows between the stranded wire cut end 112 and the ground plate 212 to thereby arc weld the wire strands at the stranded wire cut end 112 into the weld mass 114. Conductive material of the ground plate 212 is melted along with the material of the wire strands to fuse the wire strands together. Unraveling of the wire strands at the fused stranded wire cut end 212 is thereby inhibited to facilitate insertion of the stranded wire conductor through the lead body lumen and making of an electrical and mechanical connection of the fused stranded wire cut end 112 to a further lead component.

The stranded wire cut end 116 of the length 110 of stranded wire conductor 68/84/88 is then detached from first discharge terminal 204. The insulating coating 72/86/90 is stripped away to expose a segment 118 of the stranded wire conductor 68/84/88 as shown in FIG. 6. The 7×7 cable of wire strands depicted in the cross-section view of FIG. 8 do not unravel during subsequent handling, and the stripped away segment 16 can be inserted into a lumen of a lead connector element or electrode or other lead component to be affixed thereto.

It will be understood that the process of welding the stranded wire cut end 112 as described above can be advantageously used with stranded wire conductors 68/84/88 that already have an electrically conductive lead component attached by another process to the stranded wire cut end 116. In that case, the lead component would be attached to the first discharge terminal 204 in the above-described process.

It will also be understood that the process can be repeated using the weld system 200 to form a weld mass 114 between the wire strands at the stranded wire cut end 116. The cut end 116 may be trimmed back so that the insulating layer 72/86/90 extends up to the cut end 116 or may not be trimmed. Whether trimmed or not, the exposed segment 118 adjacent the fused stranded wire cut end 112 is attached to the first discharge terminal 204, and the high voltage capacitor 202 is recharged as shown in FIG. 3. The stranded wire cut end 116 is brought into close proximity or contact with the ground plate 212 to initiate discharge of the weld energy of the high voltage capacitor 202 through the stranded wire length 110 and between the stranded wire cut end 116 and the ground plate 212 to arc weld the wire strands at the stranded wire cut end 116 and metal from the ground plate 212 into a weld mass 114 in the manner described above.

The ground plate 212 is preferably formed of conductive material that is common to or the same as a material of the wire strands to ensure that no contamination is introduced in the transfer of material of the ground plate 212 into the interstices of the wire strands. For example, the ground plate 212 is preferably formed of MP35N alloy when the wire strands are formed of MP35N alloy with or without a silver core.

Advantageously, the weld energy required to transfer conductive material from the ground plate 212 into the interstices between individual wire strands to fuse the wire strands together is relatively low due to the materials and the small diameters of the wire strands. We have found that a 24 volt battery will provide sufficient energy when high voltage capacitor 202 is charged to 24 volts to deliver sufficient weld energy to the small diameter, stranded wire conductor 68/84/88 to effect the fusion of the silver core MP35N strands into the weld mass 114.

Advantageously, the low electrical resistance of such silver core wires of the stranded wire conductor ensures that the current of the electrical arc between the stranded wire cut end and the ground plate is maximized without unduly heating the stranded wire conductor itself.

Moreover, fitting of the fused wire end through a lead body lumen or into a lumen of a further lead component is not made more difficult because the diameter of the stranded wire conductor is not increased when the fusing takes place to form the weld mass.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A method of preparing a stranded wire conductor for fabrication into an electrical medical lead of the type comprising a lead body having a lead body length and lead body lumen extending between further proximal and distal lead components comprising the steps of:
    providing a stranded wire conductor formed of a plurality of wire strands formed of one or more conductive material;
    cutting the stranded wire conductor into a conductor length, whereby the stranded wire conductor has a stranded wire cut end;
    coupling the cut stranded wire conductor to a first discharge terminal of a weld energy source;
    coupling a ground plate to a second discharge terminal of the weld energy source; and
    initiating discharge of weld energy from the weld energy source between the stranded wire cut end and the ground plate inducing heat in the wire strands at the stranded wire cut end and the ground plate sufficient to transfer conductive material from the ground plate to the wire strands and fuse at least a portion of the wire strands together and inhibit unraveling of the wire strands at the fused stranded wire cut end to facilitate insertion of the stranded wire conductor through the lead body lumen and making an electrical and mechanical connection of the fused stranded wire cut end to a further lead component.

2. The method of claim 1, wherein:
    the weld energy source is a high voltage discharge capacitor disposed between said first and second discharge terminals and charged to a weld voltage; and
    the initiating step comprises disposing the stranded wire cut end in proximity with the ground plate causing the high voltage capacitor to discharge weld energy between the stranded wire cut end and the ground plate and arc weld the wire strands at the stranded wire cut end.

3. The method of claim 2, wherein the stranded wire conductor is covered with a layer of conductor insulation and the connection making step comprises removing the conductor insulation at the stranded wire cut end to expose a connection length of the stranded wire conductor adjacent the fused stranded wire cut end to facilitate connection to a further lead component.

4. The method of claim 3, wherein at least a portion of the wire strands comprise a silver core wire.

5. The method of claim 3, wherein the stranded wire conductor comprises a 7×7 cable of wire strands, and at least a portion of the wire strands comprise a silver core wire.

6. The method of claim 3, wherein the stranded wire conductor comprises a 1×19 cable of wire strands, and at least a portion of the wire strands comprise a silver core wire.

7. The method of claim 3, wherein the wire strands and the ground plate are formed of MP35N alloy.

8. The method of claim 7, wherein at least a portion of the wire strands comprise a silver core wire.

9. The method of claim 7, wherein the stranded wire conductor comprises a 7×7 cable of wire strands, and at least a portion of the wire strands comprise a silver core wire.

10. The method of claim 7, wherein the stranded wire conductor comprises a 1×19 cable of wire strands, and at least a portion of the wire strands comprise a silver core wire.

11. The method of claim 2, wherein at least a portion of the wire strands comprise a silver core wire.

12. The method of claim 2, wherein the wire strands and the ground plate are formed of MP35N alloy.

13. The method of claim 12, wherein at least a portion of the wire strands comprise a silver core wire.

14. The method of claim 12, wherein the stranded wire conductor comprises a 7×7 cable of wire strands, and at least a portion of the wire strands comprise a silver core wire.

15. The method of claim 12, wherein the stranded wire conductor comprises a 1×19 cable of wire strands, and at least a portion of the wire strands comprise a silver core wire.

16. The method of claim 1, wherein the wire strands and the ground plate are formed of MP35N alloy.

17. The method of claim 1, wherein the wire strands and the ground plate are formed having a metal in common.

18. The method of claim 17, wherein the stranded wire conductor comprises a plurality of wire strands, and at least a portion of the wire strands comprise a silver core wire.

19. The method of claim 17, wherein the stranded wire conductor comprises one of a 1×19 and 7×7 cable of wire strands, and at least a portion of the wire strands comprise a silver core wire.

* * * * *